Figure 1:
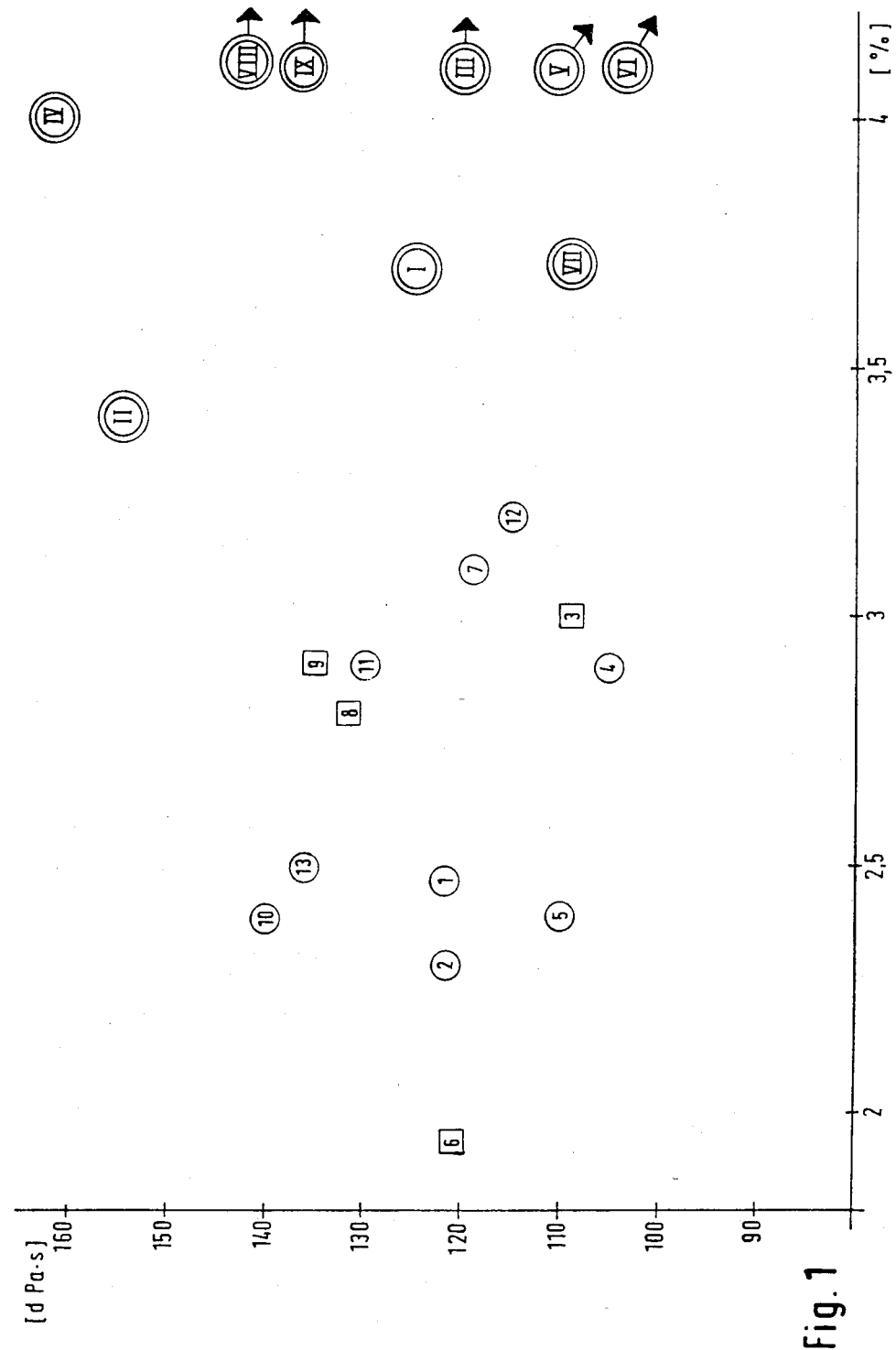

United States Patent

Sauer et al.

Patent Number: 4,722,958
Date of Patent: Feb. 2, 1988

[54] PROCESS FOR THE PREPARATION OF COPOLYMERS

[75] Inventors: Josef Sauer, Alzenau-Kälberau; Friedrich Engelhardt; Kerstine Rabas, both of Frankfurt am Main; Ulrich Karsunky, Hünfelden; Wolfram Schidlo, Hofheim-Diedenbergen; Jochen M. Quack, Eppstein; Alwin K. Reng, Kelkheim; Werner Skrypzak, Liederbach, all of Fed. Rep. of Germany

[73] Assignee: Cassella Aktiengesellschaft, Leverkusen, Fed. Rep. of Germany

[21] Appl. No.: 8,261

[22] Filed: Jan. 29, 1987

Related U.S. Application Data

[63] Continuation of Ser. No. 751,521, Jul. 3, 1985, abandoned.

[30] Foreign Application Priority Data

Jul. 24, 1984 [DE] Fed. Rep. of Germany ....... 3427220

[51] Int. Cl.[4] .................. C08F 2/06; C08F 2/10; C08F 20/58; C08K 5/05
[52] U.S. Cl. .................. 524/379; 524/389; 526/212; 526/307.6
[58] Field of Search ............ 524/379, 389; 526/212, 526/307.6

[56] References Cited

U.S. PATENT DOCUMENTS 3,336,269  8/1967  Monagle ............... 526/307.6
3,509,113  4/1970  Monagle ............... 526/307.6

Primary Examiner—Paul R. Michl
Assistant Examiner—Lee C. Wright
Attorney, Agent, or Firm—Connolly & Hutz

[57] ABSTRACT

Process for the preparation of copolymers from acrylamide and acrylic or methacrylic acid, wherein to prepare 100 parts by weight of the copolymer, (A) 10–90 parts by weight of acrylamide, (B) 90–100 parts by weight of acrylic acid and/or methacrylic acid or of a salt thereof, (C) 0–40 parts by weight of another copolymerizable monomer and (D) 0–5 parts by weight of a copolymerizable crosslinking agent which has two or more olefinic double bonds are polymerized in an alcohol having 1–4 carbon atoms by precipitation polymerization such that 10–90% by weight of the alcohol, 10–90% by weight of the total amount of monomers (A), (B) and (C) together with 100% by weight of the crosslinker substance are initially mixed, polymerization is started with 10–100% by weight of the initiator and then the remainder of the solvent, monomers, crosslinking agent and initiator to make up to 100% is metered in, as individual components or as a mixture, after the polymerization has started.

8 Claims, 1 Drawing Figure

PROCESS FOR THE PREPARATION OF COPOLYMERS

This is a continuation of application Ser. No. 751,521 filed July 3, 1985, abandoned.

The present invention relates to an improved process for the preparation of copolymers of acrylamide, acrylic acid and/or methacrylic acid and their salts and, if appropriate, a crosslinking agent and other copolymerisable monomers, in which some of the monomer mixture is initially introduced into the reaction space and, after the polymerisation has started up, the remainder of the monomers is metered into the reaction space.

Because of its variability, the process allows controlled preparation of a wide range of copolymers with specific rheological properties and, in particular, improved stability towards electrolytes. The copolymers thus obtained are outstandingly suitable as thickeners for aqueous systems, also in the presence of electrolytes.

Copolymers of acrylic acid and a polyallyl ether of a polyol with at least four C atoms and three OH groups in the molecule as a crosslinking component are known as thickeners. According to German Pat. No. 1,042,233, they are prepared by precipitation polymerisation in benzene, xylene, tetralin, hexane, heptane, carbon tetrachloride, methyl chloride, ethyl chloride and bromotrichloromethane, and mixtures of these and other solvents which are not mentioned by name. German Pat. No. 1,042,233 also describes copolymers of acrylic acid with other copolymerisable monomers, N-methylacrylamide and styrene being mentioned by name as comonomers. However, the process has the disadvantage that when the abovementioned non-polar solvents are used, polyacrylic acid suspensions over 8–10% strength can no longer be stirred.

U.S. Pat. No. 2,980,655 proposes an improvement to the abovementioned polymerisation process in the respect that by adding "polar" solvents to the solvent preferably employed, that is to say benzene (preferred polar solvents are alcohols with not more than 4 C atoms), less swelling of the polymer is observed, so that even polyacrylic acid suspensions over 18–20% strength can still be stirred. The polymerisation reaction is carried out in a closed reaction vessel in batch operation.

An improved process in comparison with U.S. Pat. No. 2,980,655 is known, from German Offenlegungsschrift No. 2,927,132, for the preparation of crosslinked polyacrylic acid and salts thereof, in which the polymerisation is carried out in accordance with the principle of precipitation polymerisation in a mixture of certain organic solvents which is free from aromatic hydrocarbons and which has a particular content of certain oxygen-containing solvents.

In particular, because of the toxicity of the benzene, cyclohexane or an aliphatic saturated hydrocarbon with 1–5 C atoms and 1–4 chlorine atoms is recommended as the non-polar component, and n-propanol or a saturated aliphatic monoalcohol with 4–6 C atoms, an aliphatic saturated carboxylic acid ester or methyl ethyl ketone is recommended as the oxygen-containing component. The crosslinked polyacrylic acids and salts thereof obtained by this process form highly viscous solutions and gels in water, but these solutions and gels still have a certain troublesome granularity and turbidity. In order to avoid these disadvantages, this known polymerisation process can also be carried out by initially introducing 50–100% by volume of the solvent mixture together with 0–100% by weight of the crosslinking monomers and metering the total amount of the acrylic acid, the amount of crosslinking monomers to make up to 100% by weight or the total amount (100% by weight) of crosslinking monomers and the amount of organic solvent mixture to make up to 100% by volume in the course of 1 to 8 hours, preferably 2 to 6 hours, into the initial mixture, which is heated at the polymerisation temperature, such that after 50% by weight of the acrylic acid has been metered in, the reaction mixture contains 60–100% by weight of the crosslinking monomer.

European Patent Application No. 69,371 describes a process for the preparation of crosslinked polyacrylic acids with improved polymerisation properties. A surfactant with a HLB value of less than 10 is added to the solvent for the precipitation polymerisation (methylene chloride is preferably employed). This leads to a more uniform grain spectrum with improved stirrability and removal of heat and less build-up of a polymer coating. U.S. Pat. No. 4,419,502 proposes a surfactant with an HLB value of greater than 12 for reducing or avoiding a coating of polymer on the walls. Methylene chloride is also claimed as the solvent in this Application.

German Offenlegungsschrift No. 3,221,284 describes a process for the preparation of a pulverulent salt of a methacrylic acid polymer by precipitation polymerisation in alcohol. Preferably, ethyl alcohol is employed, and acrylamide is also a comonomer.

To achieve certain technological properties, it is frequently necessary to mix various copolymers which have been prepared by the abovementioned known processes and have different molecular weights. Thus, for example, a company leaflet from B. F. Goodrich recommends mixing high molecular weight polyacrylic acids with low molecular weight polyacrylic acids in order to achieve a higher stability towards electrolytes when the polyacrylic acids are used as thickeners for textile printing. A similar process is described in European Patent Application No. 77,297. This publication recommends the use of a copolymer of acrylamide and acrylic acid, to which a homo-polyacrylic acid has been added, as a thickener in printing pastes for dyeing and printing fibre materials.

European Patent Application No. 48,612, in which a mixture of a gum which is more compatible with electrolytes with a polyacrylic acid as a thickener is described, is based on a similar consideration.

The known processes for the preparation of crosslinked polyacrylic acids have the considerable disadvantages and difficulties described above. Products with a high viscosity yield and adequate stability towards electrolytes can only be obtained by mixing crosslinked polyacrylic acids of different molecular weights, and in some cases with other polymers and copolymers. Furthermore, depending on the technological application, the best possible adaptation of the polymer properties to the intended use is desired. Thus, a particularly high viscosity yield may be necessary for particular purposes, and a particularly high compatibility with electrolytes may be necessary for other purposes, but it is also possible, such as, for example, when the products are used as thickeners in pigment printing, for the viscosity yield and stability towards electrolytes to be matched with one another in the most optimum manner possible.

For this intended use it is necessary, in particular, that the thickening caused by the polymer does not lead to a viscosity which is too high during the preparation of the dyestuff dispersion, since this effect makes handling of the paste very difficult, homogenisation requires an unacceptably high expenditure of energy and the fine distribution of the dyestuff which can be achieved possibly also suffers. On the other hand, after the addition of the binder (which is not to be confused with the thickener itself), which as a rule contains electrolytes, the viscosity should not fall below the minimum value required for the printing operation.

The polymerisation processes known hitherto do not allow the preparation of copolymers, in particular those built up entirely or predominantly from the monomers acrylamide and acrylic acid or methacrylic acid, which have such specific rheological properties.

There was therefore an urgent need for a polymerisation process which allows the properties of the resulting polymers to be varied within a relatively wide range and to be matched to the intended use in an optimum manner, using starting materials which are readily accessible industrially.

It has now been found that the difficulties of the known polymerisation processes can be avoided and copolymers with properties which, by the preparation process, can be varied within wide limits and can be adapted to suit the requirements are obtained if, for the preparation of 100 parts by weight of the copolymer, 10-90 parts by weight of acrylamide (monomer I), 90-10 parts by weight of acrylic acid and/or methacrylic acid and/or salts thereof with the cation $M^+$ (monomer II), 0-40 parts by weight of a copolymerisable monomer of the formula III $$R_a^3\text{—}CH_{2-a}\text{—}CH_{1-b}\text{—}R_b^3 \quad\text{(III)}$$
$$\phantom{R_a^3\text{—}CH_{2-a}\text{—}CH}|\phantom{a}$$
$$\phantom{R_a^3\text{—}CH_{2-a}\text{—}CH}X$$

and 0-5 parts by weight of a copolymerisable, known crosslinking agent which has two or more olefinic double bonds are polymerised in an alcohol with 1-4 C atoms in the manner of a precipitation polymerisation such that 10-90% by weight of the alcohol, 10-90% by weight of the total amount of monomers I and III and 10-100% by weight of the crosslinker substance are initially introduced, the polymerisation is started with 10-100% by weight of the initiator and the remainder of the solvent, monomers, crosslinking agent and initiator to make up to 100% is metered in, as individual components or as a mixture, after the polymerisation has started up.

In the abovementioned formula III of the comonomers optionally to be employed, $R^3$ denotes hydrogen or methyl, a and b each denote the value 0 or 1, the sum a+b also being 0 or 1, and X denotes a group of the formula IV $$\begin{array}{c} | \\ N\text{—}R^4 \\ | \\ COR^5 \end{array} \quad\text{(IV)}$$

wherein $R^4$ and $R^5$ independently of one another represent hydrogen, methyl or ethyl, or together represent trimethylene or pentamethylene; alkoxycarbonyl with 1 to 20, preferably 1 to 4, carbon atoms or hydroxyalkoxycarbonyl with 1 to 3 carbon atoms; N-methylolcarboxamide of the formula

HOCH$_2$NH—CO—, the methylol group of which can optionally be etherified with alkanols with 1 to 4 carbon atoms; alkanoylamino with 1 to 4 carbon atoms, which can optionally be N-substituted by methylol or alkyl with 1 to 4 carbon atoms; cyano; optionally substituted phenyl or benzyl; imidazol-1-yl; the sulphonic acid group; sulphoalkylamidocarbonyl with 1 to 4 carbon atoms in the alkyl radical; the phosphonic acid group, it also being possible for the sulphonic acid and phosphonic acid groups to be present in the form of their salts with a cation $M^+$; the phosphonic acid ester group of the formula V or the phosphonic acid anhydride group of the formula Va

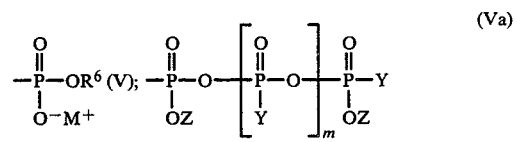

wherein $R^6$ is alkyl with 1 to 4, preferably 1 or 2, C atoms, Z has the meaning of $R^6$ or M, m is a number from 0 to 6 and Y is a radical of the formula

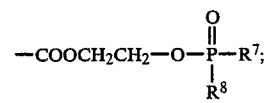

a radical of the formula VI $$-CH_{1-b}R_b^3{=}CH_{2-a}R_a^3$$

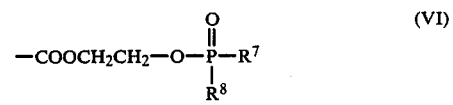

wherein $R^7$ and $R^8$ are identical or different and represent alkyl with 1 to 7, preferably 1 or 2, C atoms; a radical of the formula VII

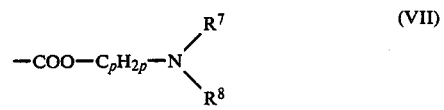

wherein $R^7$ and $R^8$ have the abovementioned meanings and p represents a number from 1 to 4; or a radical of the formula VIII

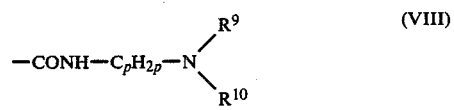

wherein $R^9$ and $R^{10}$ are identical or different and represent alkyl with 1 to 4, preferably 1 or 2, C atoms and p represents a number from 1 to 4; or one of the groups corresponding to the formulae VII and VIII which are quaternised, for example, by dimethyl sulphate or methyl chloride.

A phenyl nucleus X and the phenyl nucleus of a benzyl nucleus X are either unsubstituted or carry 1 or 2 substituents.

Suitable customary substituents are halogen and alkyl with 1 to 4 C atoms, in particular chlorine, methyl and ethyl. Monosubstitution can be in the o-, m- or p-position relative to the vinyl or allyl group, and disubstitution can preferably be in the 2,4- or 2,6-position, but also in the 2,5-, 3,5- or 3,4-position.

If X denotes phenyl or benzyl, the radicals which are only monosubstituted in the aromatic nucleus are preferred, and the unsubstituted radicals are particularly preferred.

Other substituents which a phenyl or benzyl radical X can carry are alkoxy with 1 or 2 C atoms, fluorine, trifluoromethyl or nitro.

In order to obtain the desired hydrophilic character of the copolymers according to the invention, care should be taken that at least 50% of the basic chain units contain those radicals X which have hydrophilic character and at least about 2%, preferably at least 7%, of the radicals X contain acid groups or salts thereof with the cation $M^+$.

Typical groups which have hydrophilic character are the sulphonic acid radical or carboxyl and groups X which carry these acid radicals, and carboxamide (—CO—NH$_2$) and the methylol derivative thereof, and the group of the formula IV.

Typical groups without hydrophilic character are, for example, cyano, phenyl and benzyl.

The cation $M^+$ can in principle be derived from any water-soluble known base, the strength of which is sufficient to neutralise the sulphone groups or carboxyl groups of the cross-linked copolymers according to the invention and do not impair the hydrophilicity thereof. It can thus be chosen in a simple known manner.

However, $M^+$ advantageously denotes an alkaline earth metal or, preferably, an alkali metal cation, in particular a sodium or potassium cation, ammonium or a cation derived from lower aliphatic amines. Lower aliphatic amines from which the cations $M^+$ can be derived are primary, secondary or tertiary and contain alkyl groups which have 1 to 4 C atoms and are optionally substituted by OH groups. Preferred amines are those which contain at least one α-hydroxyethyl radical, such as, for example, β-aminoethanol, β-dimethylamino-ethanol, bis-(β-hydroxyethyl)methylamine, tris-(β-hydroxyethyl)-amine, diethyl-β-hydroxyethylamine and bis-(β-hydroxyethyl)-ethylamine.

Preferred comonomers which are optionally to be employed are those of the formula III in which a is 0 and b is 1, which therefore correspond to the formula IX

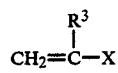

(IX)

and in which $R^3$ is hydrogen or methyl and X denotes a group of the formula IV

(IV)

wherein $R^4$ and $R^5$ independently of one another represent hydrogen methyl or ethyl or together represent trimethylene or pentamethylene; alkoxycarbonyl with 1 to 20, preferably 1 to 4, C atoms or hydroxyalkoxycarbonyl with 2 or 3, preferably 2, C atoms; the sulphonic acid group; sulphoalkylaminocarbonyl with 1 to 4 C atoms in the alkyl radical, preferably a group of the formula

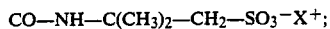

the phosphonic acid group, it also being possible for the sulphonic acid and phosphonic acid groups to be present in the form of their alkali metal or ammonium salts; or the phosphonic acid ester group of the formula V or the phosphonic acid anhydride group of the formula Va

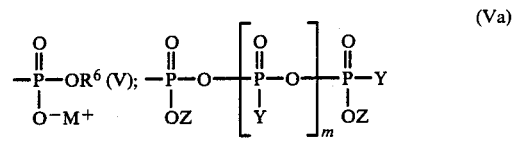

wherein $R^6$, Y, Z and m have the abovementioned meanings.

Examples of copolymerisable monomers of the formulae III and IX are N-vinyl-N-methyl-acetamide, 2-acrylamide-2-methylpropanesulphonic acid, vinylphosphonic acid, vinylphosphonic anhydride and esters of acrylic acid or methacrylic acid with alkanols with 1–20 C atoms.

According to the process of the invention copolymers are preferably prepared which are crosslinked at least to a low degree. In this case 0.2 to 5, in particular 0.5 to 2% by weight of one of the crosslinkers indicated are polymerised into the copolymer.

Compounds which have more than one olefinically unsaturated bond are employed as crosslinking agents. Allyl ethers of polyfunctional alcohols are preferably employed. Tetraallyloxyethane is particularly preferred. Esters of (meth)acrylic acid with polyfunctional alcohols are less suitable, because of their hydrolysability.

The polymerisation is carried out in a preferably watersoluble alcohol with 1–4 C atoms, such as methanol, ethanol, propanol, isopropanol and in particular in tert.-butanol.

Preferably, 30–70 parts by weight of acrylamide, 70–30 parts by weight of acrylic acid and/or methacrylic acid and 0–20 parts by weight of copolymerisable monomers of the formula III or IX, respectively, are copolymerised by the process according to the invention.

If a comonomer of formula III is used wherein X is an alkoxycarbonyl group (—COOR) with 6 to 20 C atoms, it is particularly preferred to use it in an amount of 20 to 6% by weight at the most, it being particularly appropriate for the maximum amount (maximum amount III) of this monomer to be chosen such that the following equation is satisfied:

Maximum Amount III × Number of C atoms of
—COOR group ≈ 120.

Acrylic acid and/or methacrylic acid can each be employed by themselves or in any desired mixing ratio in the copolymerisation according to the invention.

Preferably, however, methacrylic acid is employed in an amount of at most up to 30% by weight of the total amount of the acid mixture. Those copolymers prepared according to the invention which contain no methacrylic acid units are particularly preferred.

According to the process of the invention it is not only possible to polymerise a single monomer species into the copolymer but several different species of formula III. In this case the amounts given above refer to the sum of the monomeric constituents of formula III. Normally, not more than three different compounds, preferably one compound, of formula III are/is polymerised.

In view of the technological properties when the thickeners are used in textile printing and taking into consideration the price of the products, it is preferable to incorporate at most 20% of copolymerisable monomers of the formula III or IX, but in particular no such copolymerisable monomers.

The properties of the products obtained by the process according to the invention depend to a certain degree on the water content of the solvent employed. In the preparation of specific products, it is therefore advantageous to carry out the polymerisation in the presence of up to 10% by weight, preferably up to 5% by weight, of water, based on the weight of the solvent.

With water contents above 10%, there is the danger of the reaction mixture forming lumps, especially with a high (meth)acrylic acid content. The optimum water content furthermore depends on the desired field of use of the thickener. If products which are particularly stable towards electrolytes and are for use as thickeners for textile printing are to be obtained, preferably no water is used, or the water content is not more than 1% by weight. In this case, it is frequently advantageous to add up to 5% by weight of water, based on the amount of solvent, to the batch when the polymerisation has ended but before the neutralisation. In contrast, if a thickener for cosmetic purposes, with which is a particularly clear, non-granular gel is desired, is intended, preferably 2-5% by weight of water is added to the alcohol.

The amount of solvent to be employed depends on the nature of the desired copolymer, and furthermore also on the nature and amount of the monomers initially introduced and on the water content. As a rule, at most 500 g, but at least 200 g, of solvent are employed per 100 g of total monomers. The preferred amount used is between 480g and 240 g per 100 g of total monomers.

The polymerisation is as a rule carried out in a protective gas atmosphere, preferably under nitrogen. The polymerisation temperature is between 20° and 120° C., preferably between 30° and 90° C.

The polymerisation can be triggered off by using highenergy electromagnetic radiation or the usual chemical polymerisation initiators, for example organic peroxides, such as benzoyl peroxide, tert.-butyl hydroperoxide, methyl ethyl ketone peroxide, comene hydroperoxide, tert.-butyl peroxy-3,5,5-trimethylhexanoate, dicyclohexyl peroxydicarbonate and bis(4-t-butylcyclohexyl) peroxydicarbonate, azo compounds, such as azo-di-iso-butyronitrile or 2′-azo-bis-(2-amidinopropane) dihydrochloride

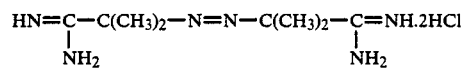

and inorganic peroxy compounds, such as $(NH_4)_2S_2O_8$, $K_2S_2O_8$ or $H_2O_2$, if appropriate in combination with reducing agents, such as sodium bisulphite and iron-II sulphate, or redox systems which contain, as the reducing component, an aliphatic or aromatic sulphinic acid, such as benzenesulphinic acid and toluenesulphinic acid or derivatives of these acids, such as, for example, Mannich adducts from sulphinic acids, aldehydes and amino compounds, such as are described in German Patent Specification No. 1,301,566. As a rule 0.03 to 2 g of the polymerisation initiator are employed per 100 g of total monomers.

The polymerisation time is as a rule 1 to 10 hours; it depends in a known manner on the polymerisation temperature and amount of initiator.

The diversity of the process allows exact adjustment of the intended production characteristics, such as viscosity yield, stability towards electrolytes and homogeneity of the aqueous solutions.

. Safety aspects, such as reliable controlability, and also economic aspects, such as a high space/time yield, can moreover also be combined with the above requirements.

The amount of monomers initially introduced depends on the requirement spectrum of the polymer. To achieve a high stability towards electrolytes, preferably 10-50% by weight of monomers I to III are initially introduced in 10 to 75% by weight of the solvent. If a high space/time yield is moreover desired in that highly concentrated polymer dispersions are to be obtained by polymerisation of monomer solutions with more than 20% by weight, in particular more than 25% by weight, of monomers, 10 to 20% by weight of the total amount of the monomers are preferably initially introduced in 10 to 50% by weight of solvent. If a high viscosity yield is also additionally important in the polymerisation of monomer solutions of above 25% by weight, 10 to 20% by weight of the total amount of monomers is preferably initially introduced in preferably 10 to 20% by weight of the total amount of the solvent. If importance is placed on the lowest possible drop after addition of electrolyte, for polymerisation of monomer solutions with more than 25% by weight of monomers, 10 to 20% by weight of the total amount of the monomers is initially introduced in preferably 20 to 50% by weight of the solvent and the remaining monomer solution to be added is correspondingly condensed. This process additionally also has the significant advantage of the possibility of better removal of heat.

The properties of the copolymers prepared according to the invention can additionally be controlled by carrying out the copolymerisation in the presence of up to 10% by weight of water, based on the total weight of the solvent.

The water content of the solvent again depends on the use spectrum. To achieve a high viscosity yield in water which is free from electrolytes, preferably 1–10% by weight of water, in particular 1–5% by weight of water, is added to the solvent. The water content is preferably divided between the initial mixture and the feed mixture such that the amount of water initially introduced is the aliquot portion to the amount of monomer initially introduced, that is to say 10–50% by weight of the total amount of water is initially introduced.

If a particularly clear, non-granular gel is desired, 2–5% by weight of water is preferably added to the solvent. The division is preferably such that the amount of water initially introduced is the aliquote portion to the amount of monomer initially introduced. If a polymer which is particularly stable towards electrolytes is desired, preferably no water is employed or the water content is not more than 1% by weight, based on the solvent. 1 to 5% by weight of water are then preferably added to the total mixture after the polymerisation but before the neutralisation.

If stability towards electrolytes, clarity, low granularity and a viscosity yield of the gels are desired, preferably 1–5% by weight of water are added; the water is divided such that preferably the amount of water initially introduced is the aliquot portion to the amount of monomer initially introduced, and 10–40% by weight of the water is particularly preferably initially introduced.

The composition of the monomers in the feed mixture and initial mixture can be varied within wide limits. With respect to the course of the polymerisation, it is preferable for at least 20% by weight of the monomers initially introduced in the initial mixture to be acrylamide. With lower acrylamide contents in the initial mixture, there is the possibility of the reaction mixture forming lumps. The composition of the monomer mixture in the initial mixture preferably does not deviate from that in the feed mixture.

The division of the crosslinking agent between the initial mixture and feed mixture is largely variable in that 10–100% by weight of the crosslinking agent, but preferably 10–50% by weight and particularly preferably an amount of the crosslinking agent which is the aliquot portion to the monomers initially introduced, can be intitially introduced. If 100% by weight of crosslinking agent is initially introduced, polymers with a higher viscosity yield and lower stability towards electrolytes are obtained. If 100% by weight of the crosslinking agent is metered in, polymers with little viscosity yield are obtained.

If highly concentrated monomer solutions are metered in, for safety reasons the initiator is preferably fed in separately, preferably as a solution. It is fed in such that the particular aliquot portion of initiator solution and monomer solution are metered in in the same unit of time. If the constituents of the feed mixture are further divided, they are preferably metered in so that in each case amounts of the other constituents of the feed mixture which are aliquot portions to the monomers fed in are added in the same unit of time.

The constituents fed in during the polymerisation are added in the course of 1 to 10 hours, preferably 1–4 hours and particularly preferably 2–4 hours. Longer feed times in general lead to higher viscosity yields. It is furthermore preferable to choose the feed rate such that an economically appropriate rate of polymerisation is ensured.

The polymerisation temperature is between 20° and 120° C., and is preferably 30°–90° C. It is particularly preferably chosen so that the initiators used have a half-life of 1–100 hours, preferably 1–50 hours.

The metering in of the initiator is effected in the customary manner such that preferably the amount of initiator which is an aliquot portion to the monomers initially introduced is initially introduced. As a rule, higher viscosity yields are thus achieved. For technological reasons, for example in order to ensure a sufficiently high rate of polymerisation, it is also possible to initially introduce more initiator, up to 100% by weight. The products thus obtained are distinguished by a lower drop in viscosity after addition of electrolytes with a lower viscosity yield.

In carrying out the polymerisation by the process according to the invention, the removal of heat presents no difficulties, even at high monomer concentrations of up to 42% by weight in the solvent, and easily stirrable polymer pastes are obtained.

The polymer pastes are entirely suitable for subsequent working up. They can be converted directly into salts with alkali metal hydroxides if the salts of acrylic acid or methacrylic acid have not been employed in the polymerisation from the start. The ammonium salts are obtained by passing in $NH_3(g)$ or by reaction with aqueous ammonia. It is even possible to employ solid alkali metal hydroxides, in which case it is particularly advantageous if the solvent contains up to 5% of water. It is also possible for the polymer to be isolated in salt or "acid" form by filtration with suction or by distilling off the solvent.

If the polymer is employed for textile printing, it is as a rule not intermediately isolated. The polymer is formulated directly as a printing paste in the salt form by distilling off the solvent and replacing it by higher-boiling isoparaffinic hydrocarbons. By choosing suitable water-in-oil emulsifiers or protective colloids, stable non-settling dispersions of the polymer in hydrocarbons are obtained. Suitable isoparaffinic hydrocarbons are known by the names ®Esso Varsol, ®Esso Exsol or ®Esso Isopar.

Suitable water-in-oil emulsifiers are as a rule sorbitan fatty acid esters, which are available under the tradenames ®Span and ®Tween. Moreover, it is also possible additionally to employ fatty acid esters, ethoxylated fatty acid esters, fatty alcohols and ethoxylated fatty alcohols, and block polymers of the ethylene oxide/propylene oxide or ethylene oxide/butylene oxide type.

It is surprising and unpredictable that a delayed addition of monomers and, if appropriate, other constituents of the polymerisation batch during the polymerisation by the process according to the invention enables the property spectrum of the resulting polymers to be substantially varied as required in a simple manner involving virtually neutral costs, and in particular leads to a drastically higher stability towards electrolytes. It is not possible to obtain products of comparable quality by two successive one-pot processes, in which first a highly crosslinked polymer and then a polymer with a lower degree of crosslinking or vice versa is prepared. Furthermore, the effect which the water content of the solvent exerts on the stability towards electrolytes is completely surprising and unpredictable.

The nature of the metering in of the initiator also has an influence on the molecular weight and the stability towards electrolytes which is completely surprising and unpredictable.

The application of the invention has particular advantages for textile printing. Besides the advantage mentioned, that the polymer does not have to be intermediately isolated, the viscosity range required for the printing can be adjusted exactly during the polymerisation. Printing pastes for pigment printing of textiles should be adjusted to a viscosity range of 60–80 dPas. However, when the thickener is stirred into water, a higher viscosity value must be accepted, this being higher the greater the sensitivity towards electrolytes of the copolymer employed as the thickener, and which then drops to the desired viscosity value of the printing paste when the customary electrolyte-containing constituents of the printing paste are added, such as, for example, binders, fixing agents, any acid donors (($NH_4$)$_2SO_4$ or ($NH_4$)$_3PO_4$) and the like.

The lowest possible starting value of the viscosity, which falls to 60–80 dPas due to the electrolyte content of the other constituents of the printing paste, is desired here. A low starting value facilitates incorporation of the other constituents of the printing paste, and homogeneous pastes can thus more easily be prepared. Thickeners with a starting viscosity above 160 dPas cannot be used, since the other constituents can then only be incorporated with difficulty. On a large industrial scale, incorporation is virtually impossible. Outstanding thickeners for pigment printing of textiles which show only a slight drop in viscosity as a result of the influence of electrolytes can be prepared by the process according to the invention. Products which are suitable for pigment printing of textiles preferably contain 30–70% by weight of acrylamide and 70–30% by weight of acrylic acid as well as 0–2% by weight of crosslinking agent.

It is of course also possible for the copolymer obtained by the process according to the invention to be isolated without prior neutralisation, that is to say in "acid" form.

The copolymers according to the invention thus prepared can preferably be employed for increasing the viscosity of and stabilising cosmetic, pharmaceutical and industrial products. For example, after neutralisation with alkalis, the substances according to the invention can be used for stabilising aqueous and/or solvent-containing emulsions, suspensions or solutions. By adding these viscosity-inducing and stabilising copolymers, predominantly in neutralised form, a substantial improvement in the physical stability as a function of the storage time and temperature is achieved in the corresponding cosmetic, pharmaceutical or industrial products.

In addition, the agents according to the invention which impart consistency also favourably influence the technological properties. For example, in the case of industrial products, improved adhesion to the substrate to be treated is achieved due to the high viscosity produced. When used in pharmaceutical or cosmetic products, the high viscosity gives rise to a more favourable ease of distribution over the hair and skin surfaces, and better adhesion of the products of the body surface.

In contrast to the customary agents which impart consistency, such as starch, gelatine, agar-agar or tragacanth, the aqueous gels based on the copolymers according to the invention are also less susceptible to attack by microorganisms. Another advantage is the favourable rheological properties as a function of the temperature. This means that even at higher storage temperatures, such as, for example, +45° C., the viscosity does not drop substantially in comparison to that at room temperature of about +20° C.

Depending on the amount of copolymer employed or the neutralising agent used, clear and completely homogeneous solutions containing no microgels can be obtained, for example, with water. A further advantage of these solutions is their favourable rheological behaviour, that is to say the corresponding products do not "draw treads". This is an essential advantage, above all, in use of the pharmaceutical, cosmetic and technical products in practice.

The formulations given in the following examples for the preparation of industrial, cosmetic and pharmaceutical products preferably contain copolymers based on 30 to 70% by weight of acrylamide, 70 to 30% by weight of acrylic acid and 0.3 to 2.5% by weight of crosslinking agent. Preferred thickeners, prepared according to the invention, for cosmetic formulations can furthermore contain up to 10% of vinylphosphonic acid or vinylphosphonic anhydride.

EXAMPLE 1

440 ml of tert.-butanol and 15 ml of deionised water are initially introduced into a polymerisation vessel equipped with a stirrer, reflux condenser, thermometer, gas inlet tube, dropping funnel with its own stirrer and electrically heated waterbath. 49.7 g of acrylamide and 21.3 g of acrylic acid are dissolved therein, with stirring, and 0.75 g of tetraallyloxyethane is then added to this solution.

440 ml of tert.-butanol and 15 ml of deionised water are initially introduced into the dropping funnel, 49.7 g of acrylamide and 21.3 g of acrylic acid are dissolved therein, with stirring, and 0.75 g of tetraallyloxyethane and 1 g of azodiisobutyronitrile are added to the solution.

The reaction vessel is warmed to 50° C., while stirring and passing in a weak stream of nitrogen, and 1 g of azodiisobutyronitrile is added at this temperature. About 10 to 30 minutes after the addition of the intiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°–70° C. in the course of 1 hour and falls again towards the end of the reaction. The polymer precipitates out of the solution, and a white mass which is very easily stirrable is obtained. When the addition of monomers has ended, the batch is stirred at an internal temperature of 80° C. for a further 2 hours.

After the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethòxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point and the solvent tert.-butanol is distilled off completely during the dropwise addition. 415 g (~100% of theory) of a pourable, non-settling, approximately 37% strength dispersion of the polymer in the hydrocarbon mixture remain.

To test the thickening action of the resulting polymer, 40 g of the 37% strength dispersion are diluted to 1,000 g with demineralised water and the dilution is stirred. Within one minute, a white viscous mass is obtained by swelling of the polymer, and is stirred for a maximum of 5 minutes, until solution is complete. The viscosity of the mass is determined as 130 dPas with a rotary viscometer, the "Haake Viskotester". 80 to 150 g of a commercially available binder, for example Imperon Binder MTB, are added to 850 to 920 g of the previously prepared mass, with stirring. As a result of the electrolyte content of the binder, the viscosity of the system falls to 80 dPas. The same drop is observed if a solution of 1.1 g of ammonium sulphate in 2.2 g of demineralised $H_2O$ (an acid donor frequently employed in pigment printing), or a solution of 1.1 g of sodium chloride in 5 ml of demineralised water is added, with stirring, to 1,000 g of the mass prepared.

A simple possiblity for obtaining characteristic data for the thickening action of the copolymer dispersions prepared comprises determining the viscosities in pure water and in an approximately 0.11% strength by weight ammonium sulphate or sodium chloride solution at several different polymer concentrations.

In order to obtain directly comparable numerical values for the thickening action of the copolymers prepared, the % by weight of 37% strength dispersion required to obtain a certain viscosity of, for example, 70 dPas in one of the abovementioned electrolyte solutions and the level to which the viscosity in pure water increases with the same amount of dispersion can then, for example, be stated. In the present example, 2.86% by weight (2.9 g of dispersion+97.1 g of electrolyte solution) of the 37% strength polymer dispersion must be added to establish a viscosity of 70 dPas in the 0.11% strength by weight ammonium sulphate solution.

The same amount of polymer added to pure water then leads to a viscosity of 119 dPas.

In the following embodiment and comparison examples and in the tabular examples, the data scheme given below is used for characterisation:

| Viscosity of the electrolyte solution in dPas | Concentration of 37% strength polymer solution in the electrolyte solution required to establish this viscosity | Viscosity which results when the same polymer concentration is established in pure water, in dPas |
| --- | --- | --- |

For the above example, this data scheme has the values 70/2.86–119.

Embodiment Example 1 is repeated with the modification that the neutralisation with ammonia is omitted, and instead 23.6 g of solid powdered sodium hydroxide are stirred into the batch. Stirring is continued further until the sodium hydroxide has dissolved completely, and then working up is continued as described above. 420 g of copolymer dispersion no. 14 in Table 1, according to the invention, with the characteristic data 70/2.47–123 are obtained.

EXAMPLE 2

440 ml of tert.-butanol are initially introduced into a polymerisation vessel equipped with a stirrer, reflux condenser, thermometer, gas inlet tube, dropping funnel with its own stirrer and electrically heated waterbath. 49.7 g of acrylamide and 21.3 g of acrylic acid are dissolved therein, with stirring, and 0.75 g of tetraallyloxyethane is then added to this solution.

440 ml of tert.-butanol are initially introduced into the dropping funnel, 49.7 g of acrylamide and 21.3 g of acrylic acid are dissolved therein, with stirring, and 0.75 g of tetraallyloxyethane and 1 g of azodiisobutyronitrile are added to the solution.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°–70° C. in the course of 1 hour and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge, a solution of 7.0 g of a sorbitan fatty acid ester, 9.8 g of an ethoxylated nonylphenol and 2.8 g of an ethylene oxide/propylene oxide block polymer in 239.0 g of isoparaffinic hydrocarbon mixture with a boiling range of 150° to 350° C. is added dropwise through the dropping funnel. The reaction mixture is at the same time heated to the boiling point and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.3–123.

EXAMPLE 3

400 ml of tert.-butanol are initially introduced into a polymerisation vessel equipped with a stirrer, reflux condenser, thermometer, gas inlet tube, dropping funnel with its own stirrer and electrically heated waterbath. 21.3 g of acrylamide and 49.7 g of acrylic acid are dissolved therein, with stirring, and 1.2 g of tetraallyloxyethane are then added to this solution.

440 ml of tert.-butanol are initially introduced into the dropping funnel, 21.3 g of acrylamide and 49.7 g of acrylic acid are dissolved therein, with stirring, and 1.2 g of tetrallyloxyethane and 1 g of tert.-butyl peroxy-3,5,5-trimethylhexanoate are added to the solution.

The reaction vessel is warmed to 80° C., while stirring and passing in a weak stream of nitrogen, and 1 g of tert.-butyl peroxy-3,5,5-trimethylhexanoate, dissolved in 40 ml of tert.-butanol, is added at this temperature. About 10 to 30 minutes after the addition of the initiator, the polymerisation starts with a clear rise in temperature. As soon as the temperature in the reaction vessel has risen by about 2° C., the monomer solution is uniformly added dropwise from the dropping funnel in the course of 2 hours. The polymerisation temperature rises immediately to 82° C. The polymer precipitates out of the solution, and a white mass which is very easily stirrable is obtained. When the addition of the monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/3–108.

EXAMPLE 4

90 ml of tert.-butanol are initially introduced into a polymerisation vessel equipped with a stirrer, reflux condenser, thermometer, gas inlet tube, two dropping funnels with their own stirrer and an electrically heated waterbath. 9.9 g of acrylamide and 4.2 g of acrylic acid are dissolved therein, with stirring, and 0.15 g of tetraallyloxyethane and 0.5 g of bis-(4-tert.-butyl-cyclohexyl) peroxydicarbonate are then added to this solution.

450 ml of tert.-butanol are initially introduced into the first dropping funnel, 89.5 g of acrylamide and 38.4 g of acrylic acid are dissolved therein, with stirring, and 1.35 g of tetraallyloxyethane are added to the solution. 0.5 of bis-(4-tert.-butyl-cyclohexy) peroxydicarbonate, dissolved in 40 ml of tert.-butanol, are introduced into the second dropping funnel.

The reaction vessel is warmed to 48° C., while stirring and passing in a weak stream of nitrogen. After about 10 to 30 minutes, the polymerisation starts, with a clear rise in temperature. As soon as the temperature in the reaction vessel has risen by about 3° C., the monomer solution from the first dropping funnel and the initiator solution from the second dropping funnel are uniformly added dropwise in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.2–115.

If only 0.1 g of initiator is initially introduced and 0.9 g are metered in after the start of the polymerisation, a copolymer according to the invention with the characteristic data: 70/2.0–130 is obtained.

EXAMPLE 5

176 ml of tert.-butanol and 6 ml of deionised water are initially introduced into a polymerisation vessel equipped with a stirrer, reflux condenser, thermometer, gas inlet tube, dropping funnel with its own stirrer and electrically heated waterbath. 19.9 g of acrylamide and 8.5 g of acrylic acid are dissolved therein, with stirring, and 0.3 g of tetraallyloxyethane is then added to this solution.

704 ml of tert.-butanol and 24 ml of deionized water are initially introduced into the dropping funnel, 79.5 g of acrylamide and 34.1 g of acrylic acid are dissolved therein, with stirring, and 1.2 g of tetraallyloxyethane and 1.6 g of bis-(4-tert.-butyl-cyclohexyl) peroxydicarbonate are added to the solution.

The reaction vessel is warmed to 48° C., while stirring and passing in a weak stream of nitrogen, and 0.4 g of bis-(4-tert.-butyl-cyclohexyl) peroxydicarbonate is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.4–110.

By varying the above experimental conditions in the manner shown in Table 1, copolymer dispersions 15 and 16 according to the invention, which are likewise very advantageous, can be prepared.

EXAMPLE 6

440 ml of tert.-butanol and 15 ml of deionised water are initially introduced into a polymerisation vessel equipped with a stirrer, reflux condenser, thermometer, gas inlet tube, dropping funnel with its own stirrer and electrically heated waterbath. 35.5 g of acrylamide, 21.3 g of acrylic acid and 14.2 g of 2-acrylamido-2-methylpropanesulphonic acid are dissolved therein, with stirring, and 0.75 g of tetraallyloxyethane is then added to this solution.

440 ml of tert.-butanol and 15 ml of deionized water are initially introduced into the dropping funnel, 35.5 g of acrylamide, 21.3 g of acrylic acid and 14.2 g of 2-acrylamido-2-methylpropanesulphonic acid are dissolved therein, with stirring, and 0.75 g of tetraallyloxyethane and 1.0 g of azodiisobutyronitrile are added to the solution.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.51–122.

EXAMPLE 7

88 ml of tert.-butanol and 3 ml of deionized water are initially introduced into a polymerisation vessel equipped with a stirrer, reflux condenser, thermometer, gas inlet tube, dropping funnel with its own stirrer and electrically heated waterbath. 9.9 g of acrylamide and 4.3 g of acrylic acid are dissolved therein, with stirring, and 0.15 g of tetraallyloxyethane is then added to this solution.

792 ml of tert.-butanol and 27 ml of deionised water are initially introduced into the dropping funnel, 89.5 g of acrylamide and 38.3 g of acrylic acid are dissolved therein, with stirring, and 1.35 g of tetraallyloxyethane and 1.8 g of azodiisobutyronitrile are added to the solution.

The reaction vessel is warmed to 58° C., while stirring and passing in a weak stream of nitrogen, and 0.2 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/3.1–118.

By varying the experimental conditions in the manner shown in Table 1, copolymers Nos. 17 and 18 are obtained.

EXAMPLE 8

400 ml of tert.-butanol and 10 ml of deionised water are initially introduced into a polymerisation vessel equipped with a stirrer, reflux condenser, thermometer, gas inlet tube, dropping funnel with its own stirrer and electrically heated waterbath. 42.6 g of acrylamide and 28.4 g of acrylic acid are dissolved therein, with stirring, and 0.6 g of tetraallyloxyethane is then added to this solution.

440 ml of tert.-butanol and 10 ml of deionised water are initially introduced into the dropping funnel, 42.6 g of acrylamide and 28.4 g of acrylic acid are dissolved therein, with stirring, and 0.6 g of tetraallyloxyethane and 1 g of tert.-butyl peroxy-3,5,5-trimethylhexanoate are added to the solution.

The reaction vessel is warmed to 80° C. while stirring and passing in a weak stream of nitrogen, and 1 g of tert.-butyl peroxy-3,5,5-trimethylhexanoate, dissolved in 40 ml of tert.-butanol, is added at this temperature. About 10 to 30 minutes after the addition of the initiator, the polymerisation starts, with a clear rise in temperature. As soon as the temperature in the reaction vessel has risen by about 2° C., the monomer solution is uniformly added dropwise from the dropping funnel in the course of 2 hours. The polymerisation temperature immediately rises to 82° C., the polymer precipitates out of the solution and a white mass which is very easily stirrable is obtained. When the addition of monomers has ended, the batch is stirred at an internal temperature of 80° C. for a further 2 hours.

When the reaction mixture has cooled to 20° C., it is neutralised by passing the gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-setting, approximately 37% strength dispersion of the polymer in the hydrocarbon mixture remain. Characteristic data: 70/2.62–127.

By varying the above experimental conditions in the manner shown in Table 1, copolymer dispersion 19 according to the invention, which is likewise very advantageous, can be prepared.

EXAMPLE 9

440 ml of tert.-butanol and 10 ml of deionised water are initially introduced into a polymerisation vessel equipped with a stirrer, reflux condenser, thermometer, gas inlet tube, dropping funnel with its own stirrer and electrically heated waterbath. 35.5 g of acrylamide and 35.5 g of acrylic acid are dissolved therein, with stirring, and 1 g of tetraallyloxyethane is then added to this solution.

440 ml of tert.-butanol and 10 ml of deionised water are initially introduced into the dropping funnel, 35.5 g of acrylamide and 35.5 g of acrylic acid are dissolved therein, with stirring, and 1 g of tetraallyloxyethane and 1 g of azodiisobutyronitrile are added to the solution.

The reaction vessel is warmed to 40° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 60° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.9–135.

EXAMPLE 10

68 ml of tert.-butanol and 3 ml of deionised water are initially introduced into a polymerisation vessel equipped with a stirrer, reflux condenser, thermometer, gas inlet tube, dropping funnel with its own stirrer and electrically heated waterbath. 9.94 g of acrylamide and 4.26 g of acrylic acid are dissolved therein, with stirring, and 0.15 g of tetraallyloxyethane is then added to this solution.

540 ml of tert.-butanol and 27 ml of deionised water are initially introduced into the dropping funnel, 89.5 g of acrylamide and 38.34 g of acrylic acid are dissolved therein, with stirring, and 1.35 g of tetraallyloxyethane are added to the solution. 1.8 g of bis-(4-tert.-butyl-cyclohexyl)peroxydicarbonate are dissolved in 72 ml of tert.-butanol in a second dropping funnel.

The reaction vessel is warmed to 48° C., while stirring and passing in a weak stream of nitrogen, and 0.2 g of bis-(4-tert.-butyl-cyclohexyl)peroxydicarbonate is added at this temperature. About 10 to 30 minutes after the addition of the initiator, the polymerisation starts, with a clear rise in temperature. As soon as the temperature in the reaction vessel has risen by about 3° C., the monomer solution and the initiator solution are uniformly added dropwise from the dropping funnels in the course of 2 hours. The polymerisation temperature rises to 55° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.4–140.

EXAMPLE 11

630 ml of tert.-butanol and 15 ml of deionised water are initially introduced into a polymerisation vessel equipped with a stirrer, reflux condenser, thermometer, gas inlet tube, dropping funnel with its own stirrer and electrically heated waterbath. 49.7 g of acrylamide and 21.3 g of acrylic acid are dissolved therein, with stirring, and 0.6 g of tetraallyloxyethane is then added to this solution.

150 ml of tert.-butanol and 15 ml of deionised water are initially introduced into the dropping funnel, 49.7 g of acrylamide and 21.3 g of acrylic acid are dissolved therein, with stirring, and 1.4 g of tetraallyloxyethane are added to the solution. 1 g of azodiisobutyronitrile is dissolved in 100 ml of tert.-butanol in a second dropping funnel.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution and the initiator solution are uniformly added dropwise from the dropping funnels in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/2.9–130.

By varying the above experimental conditions in the manner shown in table 1, copolymer dispersions 20 and 21 according to the invention, which are likewise very advantageous, can be prepared.

EXAMPLE 12

630 ml of tert.-butanol and 15 ml of deionised water are initially introduced into a polymerisation vessel equipped with a stirrer, reflux condenser, thermometer, gas inlet tube, dropping funnel with its own stirrer and electrically heated waterbath. 49.7 g of acrylamide and 21.3 g of acrylic acid are dissolved therein, with stirring, and 1 g of tetraallyloxyethane, as a crosslinking agent, and 0.04 g of dodecylmercaptan, as a regulator, are added to this solution.

150 ml of tert.-butanol and 15 ml of deionised water are initially introduced into the dropping funnel, 49.7 g of acrylamide and 21.3 g of acrylic acid are dissolved therein, with stirring, and 1 g of tetraallyloxyethane is added to the solution. 1 g of azodiisobutyronitrile is dissolved in 100 ml of tert.-butanol in a second dropping funnel.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution and the initiator solution are uniformly added dropwise from the dropping funnels in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

The reflux condenser is replaced by a distillation bridge and a solution of 7.0 g of a sorbitan fatty acid ester, 9.8 g of an ethoxylated nonylphenol and 2.8 g of an ethylene oxide/propylene oxide block polymer in 239.0 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. 415 g (~100% of theory) of a pourable, non-settling, approximately 37% strength dispersion of the polymer in the hydrocarbon mixture remain. Characteristic data: 70/3.2–115.

By dividing the regulator substance between the initial mixture and the feed mixture, copolymer dispersion 22 according to the invention, which is likewise very advantageous and is shown in Table 1, can be prepared.

EXAMPLE 13

440 ml of tert.-butanol are initially introduced into a polymerisation vessel equipped with a stirrer, reflux condenser, thermometer, gas inlet tube, dropping funnel with its own stirrer and electrically heated waterbath. 49.7 g of acrylamide and 21.3 g of acrylic acid are dissolved therein, with stirring, and 1.0 g of tetraallyloxyethane is then added to this solution. 20 ml of 25% strength by weight aqueous ammonia solution are then added.

440 ml of tert.-butanol are initially introduced into the dropping funnel, 49.7 g of acrylamide and 21.3 g of acrylic acid are dissolved therein, with stirring, and 1.0 g of tetraallyloxyethane and 1 g of azodiisobutyronitrile are added to the solution. Thereafter, 20 ml of 25% strength by weight aqueous ammonia solution are also added.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°–70° C. in the course of 1 hour, and drops again towards the end of the reaction. The polymer precipitates out of the solution, and a white mass which is very easily stirrable is obtained. When the addition of monomers has ended, the batch is stirred at an internal temperture of 80° C. for a further 2 hours.

When the reaction mixture has cooled to 20° C., the polymerisation vessel is equipped with a homogenising apparatus and the polymer dispersion is thoroughly homogenised by pumping several times over the homogenising apparatus.

For working up and distilling off the tert.-butanol, 7 g of a sorbitan fatty acid ester, 9.8 g of an ethoxylated nonylphenol and 2.8 g of an ethylene oxide/propylene oxide block polymer dissolved in 360 g of an isoparaffinic hydrocarbon mixture with a boiling range of 150° to 350° C. are added dropwise to the polymer paste and the tert.-butanol is then distilled off. About 534 g (~100% of theory) of a pourable, non-settling, approximately 29% strength dispersion of the polymer in the hydrocarbon mixture remain.

Characteristic data: (converted to 37% strength by weight dispersion) 70/2.49-136.5.

By varying the experimental conditions in accordance with the data in the following Table 1, copolymers nos. 23 to 32 according to the invention are also obtained. The following abbreviations are used in Table 1:

A = azodiisobutyronitrile
B = bis-(4-tert.-butyl-cyclohexyl)peroxydicarbonate
C = tert.-butyl peroxy-3,5,5-trimethylhexanoate
R = dodecylmercaptan (regulator)
TAE = tetraallyloxyethane
TPTA = trimethylolpropane trimethacrylate
(a) = dissolved in 100 ml of tert.-butanol
(b) = dissolved in 80 ml of tert.-butanol
(c) = dissolved in 72 ml of tert.-butanol

EXAMPLE 33

440 ml of tert.-butanol and 10 ml of deionised water are initially introduced into a polymerisation vessel equipped with a stirrer, reflux condenser, thermometer, gas inlet tube, dropping funnel with its own stirrer and electrically heated waterbath. 35.5 g of acrylamide and 35.5 g of acrylic acid are dissolved therein, with stirring, and 1.0 g of tetraallyloxyethane is then added to this solution.

440 ml of tert.-butanol and 10 ml of deionised water are initially introduced into the dropping funnel, 35.5 g of acrylamide and 35.5 g of acrylic acid are dissolved therein, with stirring, and 1.0 g of tetraallyloxyethane and 1 g of azodiisobutyronitrile are added to the solution.

The reaction vessel is warmed to 50° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 55°-60° C. in the course of 1 hour, and drops

TABLE 1

| | Initial mixture | | | | | | | | | Feed mixture | | | | | | | | Characteristic data |
|---|---|---|---|---|---|---|---|---|---|---|---|---|---|---|---|---|---|---|
| No. | AM (g) | AA (g) | Reg. (g) | TAE (g) | Init. | Init. (g) | t. Bu (ml) | H$_2$O (ml) | Temp. (°C.) | AM (g) | AA (g) | Reg. III (g) | TAE (g) | Init. | Init. (g) | t. Bu (ml) | H$_2$O (ml) | |
| 14 | 49,7 | 21,3 | | 0.75 | A | 1,0 | 630 | 15 | 50 | 49,7 | 21,3 | | 0,75 | A | 1,0 | 150 | 15 | 70/2,47-123 |
| 15 | 9,94 | 4,26 | — | 0,15 | B | 0,2 | 88 | 3 | 51 | 89,5 | 38,3 | — | 1,35 | B | 1,8 | 792 | 27 | 70/2,6-108 |
| 16 | 19,9 | 8,5 | — | 0,3 | A | 0,4 | 176 | 6 | 58 | 79,5 | 34,1 | — | 1,2 | A | 1,6 | 704 | 24 | 70/2,4-100 |
| 17 | 29,8 | 12,8 | — | 0,45 | A | 0,4 | 264 | 9 | 56 | 69,6 | 29,8 | — | 1,05 | A | 1,4 | 616 | 21 | 70/2,7-139 |
| 18 | 59,6 | 25,6 | — | 0,9 | B | 1,0 | 528 | 18 | 48 | 39,8 | 17,0 | — | 0,6 | B | 0,8 | 352 | 12 | 70/3,2-99 |
| 19 | 49,7 | 21,3 | — | 0,43 | C | 1,0 | 400 | 15 | 80 | 49,7 | 21,3 | — | 0,43 | C | 1,0 | 440 | 15 | 70/1,7-123 |
| 20 | 49,7 | 21,3 | — | 0,7 | A | 1,0 | 630 | 15 | | 49,7 | 21,3 | — | 1,3 | A | 1,0(a) | 150 | 15 | 70/2,9-135 |
| 21 | 49,7 | 21,3 | — | 0,75 | A | 1,0 | 630 | 15 | 50 | 49,7 | 21,3 | — | 1,25 | A | 1,0(a) | 150 | 15 | 70/3,0-132 |
| 22 | 49,7 | 21,3 | R 0,02 | 1,0 | A | 1,0 | 650 | 15 | 50 | 49,7 | 21,3 | R 0,02 | 1,0 | A | 1,0(b) | 150 | 15 | 70/2,9-135 |
| 23 | 49,7 | 21,3 | — | 1,0 | A | 2,0 | 730 | 15 | 50 | 49,7 | 21,3 | — | 1,0 | — | — | 150 | 15 | 70/3,6-115 |
| 24 | 49,7 | 21,3 | R 0,01 | 1,0 | A | 1,0 | 650 | 15 | 50 | 49,7 | 21,3 | R 0,01 | 1,0 | A | 1,0(b) | 150 | 15 | 70/3,0-137 |
| 25 | 49,7 | 21,3 | — | 1,0 | A | 1,0 | 630 | 15 | 50 | 49,7 | 21,3 | R 0,04 | 1,0 | A | 1,0(a) | 150 | 15 | 70/3,0-126 |
| 26 | 49,7 | 21,3 | — | 0,5 | A | 1,0 | 630 | 15 | 50 | 49,7 | 21,3 | — | 1,5 | A | 1,0(a) | 150 | 15 | 70/3,3-123 |
| 27 | 42,6 | 28,4 | — | 0,75 | A | 1,0 | 630 | 15 | 50 | 56,8 | 14,2 | — | 1,25 | A | 1,0(a) | 150 | 15 | 70/3,1-138 |
| 28 | 28,4 | 42,6 | — | 0,6 | A | 1,0 | 630 | 15 | 50 | 71 | — | — | 1,4 | A | 1,0(a) | 150 | 15 | 70/2,9-140 |
| 29 | 28,4 | 42,6 | — | 1,2 | C | 1,0 | 440 | — | 80 | 28,4 | 42,6 | — | 1,2 | C | 1,0 | 440 | — | 70/3,1-143 |
| 30 | 28,4 | 42,6 | — | 0,6 | C | 1,0 | 440 | 10 | 80 | 28,4 | 42,6 | — | 0,6 | C | 1,0 | 440 | 10 | 70/2,9-150 |
| 31 | 9,9 | 4,3 | — | TAE 0,0125 TPTA 0,05 | B | 0,1 | 58 | 3 | 46 | 89,5 | 38,3 | — | TAE 0,675 TPTA 0,45 | B | 0,9(c) | 450 | 27 | 70/2,6-145 |
| 32 | 69,6 | 29,8 | — | 1,05 | B | 1,4 | 616 | 21 | 48 | 29,8 | 12,8 | — | 0,45 | B | 0,6 | 264 | 9 | 70/3,4-95 | again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., the polymer is dried by distilling off the tert.-butanol. A loose white powder is obtained. Solutions of the polymer in demineralised water, which are obtained by stirring in the desired percentage of the polymer and adjusting the pH value to pH 7-9 with a suitable base, are distinguished by an outstanding clarity. No microgelatinous structures can be seen and the solutions are completely homogeneous.

Characteristic data: 0.1% strength solution, pH 8-8.5, 1,070 mPas, Haake VT 23; 0.2% strength solution, pH 8-8.5, 4,600 mPas, Haake VT 23; 0.5% strength solution, pH 8-8.5, 24,000 mPas, Haake VT 23.

Examples of suitable bases for adjusting the pH value are ammonia, sodium hydroxide, potassium hydroxide, sodium and potassium carbonate, sodium and potassium bicarbonate, sodium and potassium phosphate and sodium and potassium borate. They can be employed as pure solid substances ($NH_3$ in gaseous form) or as solutions in the usual concentrations.

EXAMPLE 34

Example 33 is repeated, but the polymerisation is started at 40° C. with bis-(4-tert.-butyl-cyclohexyl)-peroxydicarbonate, and the polymer which precipitates is filtered off with suction and dried. It is an excellent thickener, solutions of which are clear and have no microgel structure. It is therefore particularly suitable for cosmetic formulations.

Characteristic data: 0.1% strength solution, pH 8-8.5, 900 mPas, Haake VT 23; 0.2% strength solution, pH 8-8.5, 6,120 mPas, Haake VT 23; 0.5% strength solution, pH 8-8.5, 36,400 mPas, Haake VT 23.

EXAMPLE 35

Example 33 is repeated, but the polymerisation is carried out at 30° C. 143 g (~100% of theory) of an excellent thickener for cosmetic purposes is obtained.

Characteristic data: 0.1% strength solution, pH 8-8.5, 2,750 mPas, Haake VT 23; 0.2% strength solution, pH 8-8.5, 11,600 mPas, Haake VT 23; 0.5% strength solution, pH 8-8.5, 32,900 mPas, Haake VT 23.

EXAMPLE 36

440 ml of tert.-butanol and 10 ml of deionised water are initially introduced into a polymerisation vessel equipped with a stirrer, reflux condenser, thermometer, gas inlet tube, dropping funnel with its own stirrer and electrically heated waterbath. 32 g of acrylamide, 32 g of acrylic acid and 7.1 g of vinylphosphonic acid are dissolved therein, with stirring, and 1.0 g of tetraallyloxyethane is then added to this solution.

440 ml of tert.-butanol and 10 ml of deionised water are initially introduced into the dropping funnel, 32 g of acrylamide, 32 g of acrylic acid and 7.1 g of vinylphosphonic acid are dissolved therein, with stirring, and 1 g of tetraallyloxyethane and 1 g of azodiisobutyronitrile are added to the solution.

The reaction vessel is warmed to 58° C., while stirring and passing in a weak stream of nitrogen, and 1 g of azodiisobutyronitrile is added at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°-70° C. in the course of 1 hour, and drops again towards the end of the reaction. The polymer precipitates out of the solution, and a white mass which is very easily stirrable is obtained. When the addition of monomers has ended, the batch is stirred at an internal temperature of 80° C. for a further 2 hours.

When the reaction mixture has cooled to 20° C., the polymer is dried by distilling off the tert.-butanol. A loose white powder is obtained. Solutions of the polymer in demineralised water, which are obtained by stirring in the desired percentage of the polymer and adjusting the pH value to pH 7-9 with a suitable base, are distinguished by an outstanding clarity. No microgelatinous structures can be seen and the solutions are completely homogeneous.

Characteristic data: 0.1% strength solution, pH 8-8.5, 2,750 mPas, Haake VT 23; 0.2% strength solution, pH 8-8.5, 12,800 mPas, Haake VT 23; 0.5% strength solution, pH 8-8.5, 30,000 mPas, Haake VT 23.

EXAMPLE 37

90 ml of tert.-butanol and 2 ml of deionised water are initially introduced into a polymerisation vessel equipped with a stirrer, reflux condenser, thermometer, gas inlet tube, dropping funnel with its own stirrer and electrically heated waterbath, and 9.9 g of acrylamide, 4.2 g of acrylic acid and 0.15 g of tetraallyloxyethane, as a crosslinking agent, are dissolved therein.

450 ml of tert.-butanol and 18 ml of deionised water are initially introduced into the dropping funnel, and 89.5 g of acrylamide, 38.4 g of acrylic acid and 1.35 g of tetraallyloxyethane are dissolved therein. 0.5 g of bis-(4-tert.-butyl-cyclohexyl)peroxydicarbonate is dissolved in 40 ml of butanol in a second dropping funnel.

The reaction vessel is warmed to 46° C., while stirring and passing in a weak stream of nitrogen, and 0.5 g of bis-(4-tert.-butyl-cyclohexyl)peroxydicarbonate is added to the initially introduced reactant mixture at this temperature. About 10 to 30 minutes after the addition of the initiator, the polymerisation starts, with a clear rise in temperature. As soon as the temperature in the reaction vessel has risen by about 3° C., the monomer solution is uniformly added dropwise from the dropping funnel in the course of 2 hours. The polymerisation temperature rises to 65°-70° C. in the course of 1 hour and drops again towards the end of the reaction. The polymer precipitates out of the solution and a white mass which is very easily stirrable is obtained. When the addition of monomers has ended, the batch is stirred at an internal temperature of 80° C. for a further 2 hours.

When the reaction mixture has cooled to 20° C., it is neutralised by passing in gaseous ammonia. The temperature thereby rises to about 40° C. The polymerisation vessel is equipped with a homogenising apparatus. The polymer dispersion is thoroughly homogenised by pumping several times over the homogenising apparatus.

Further working up is effected in accordance with the statements in the above Example 6.

A 37% strength by weight polymer dispersion with the following characteristic data: 70/2.4→160 is obtained.

The copolymers according to the invention shown in the following Table 2 can also be prepared in an analogous manner.

In Examples 38 to 44, 134 g of a paraffinic hydrocarbon mixture with a boiling range of 200°–400° C. are employed as the mineral oil.

In Examples 37 to 41, 20 g of water are added to the reaction mixture after the end of the polymerisation and before the neutralisation.

In Example 41, the feed mixture is added in the course of four hours.

In the examples shown in Table 2, the initiator contained in the feed mixture is always dissolved in 40 ml of tert.-butanol and metered in through a separate dropping funnel.

TABLE 2

| | Initial mixture | | | | | | | | | Feed mixture | | | | | | | | Characteristic data |
|---|---|---|---|---|---|---|---|---|---|---|---|---|---|---|---|---|---|---|
| No. | AM (g) | AA (g) | Reg. III (g) | TAE (g) | Initi. | Initi. (g) | t. BuOH (ml) | $H_2O$ (ml) | Temp. (°C.) | AM (g) | AA (g) | Reg. (g) | TAE (g) | Initi. | Initi. (g) | t. Bu (ml) | $H_2O$ (ml) | |
| 37 | 9.9 | 4.2 | — | 0.15 | B | 0.5 | 90 | — | 48 | 89.5 | 38.4 | — | 1.35 | B | 0.5 | 450 | — | 70/2.2–146 |
| 38 | 9.9 | 4.2 | — | 0.15 | B | 0.5 | 90 | — | 48 | 89.5 | 38.4 | — | 1.35 | B | 0.5 | 450 | — | 70/1.6–150 |
| 39 | 9.9 | 4.2 | — | 0.15 | B | 0.5 B | 180 | — | 46 | 89.5 | 38.4 | — | 1.35 | B | 0.5 | 360 | — | 70/1.65–128 |
| 40 | 9.9 | 4.2 | — | 0.15 | B | 0.5 B | 270 | — | 46 | 89.5 | 38.4 | — | 1.35 | B | 0.5 | 270 | — | 70/2.5–96 |
| 41 | 9.9(1) | 4.2 | — | 0.15 | B | 0.5 B | 270 | — | 46 | 89.5 | 38.4 | — | 1.35 | B | 0.5 | 270 | — | 70/2.1–122 |
| 42 | 9.9 | 4.2 | — | 0.15 | B | 0.5 B | 270 | 9.2 | 46 | 89.5 | 38.4 | — | 1.35 | B | 0.5 | 270 | 10.8 | 70/1.7–110 |
| 43 | 9.9 | 4.2 | — | 0.15 | A | 0.5 A | 270 | 9.2 | 65 | 89.5 | 38.5 | — | 1.35 | A | 0.5 | 270 | 10.8 | 70/2.04–129 |
| 44 | 9.9 | 4.2 | — | 0.15 | B | 0.5 B | 270 | 2.0 | 46 | 89.5 | 38.5 | — | 1.35 | B | 0.5 | 270 | 18 | 70/2.0–108 |

By varying the comonomers, the crosslinker content, the initiator content and the water content the polymers of table III are obtained. Working up is effected in accordance with Example 6.

The following abbreviations are additionally used in table III:
IBMA = Isobutoxymethylene acrylamide
MAS - C18 = Methacrylic acid stearyl ester
AS - Butylester = Acrylic acid butyl ester

| | Initial mixture | | | | | | | |
|---|---|---|---|---|---|---|---|---|
| No. | AS (g) | AM (g) | Monomer III (g) | TAE (g) | Initiator (g) | t-BuOH (ml) | $H_2O$ (ml) | Temp. (°C.) |
| 45 | 21.3 | 42.6 | IBMA 7.1 | 0.75 | A 1.0 | 440 | 15 | 50 |
| 46 | 21.3 | 46.15 | IBMA 3.55 | 0.75 | A 1.0 | 440 | 15 | 50 |
| 47 | 21.3 | 48.2 | IBMA 1.5 | 0.75 | A 1.0 | 440 | 15 | 50 |
| 48 | 21.3 | 39.76 | IBMA 7.1/ MAS-C18 2.84 | 0.75 | A 1.0 | 440 | 15 | 50 |
| 49 | 11.36 | 17.04 | O | 0.15 | 0.2 Lauroylperoxide | 393 | 10 | 80 |
| 50 | 21.3 | 46.86 | MAS-C18-Ester 2.84 | 0.75 | A 1.0 | 440 | 15 | 50 |
| 51 | 4.26 | 9.69 | MAS-C18-Ester 0.28 | 0.15 | B 0.1 | 250 | 1 | 45 |
| 52 | 4.26 | 8.52 | AS—Butylester 1.42 | 0.13 | B 0.1 | 254 | 2 | 45 |
| 53 | 4.26 | 8.52 | AS—Butylester 1.42 | 0.13 | B 0.1 | 254 | 0 | 45 |
| 54 | 5.68 | 5.02 | AS—Butylester 3.5 | 0.15 | B 0.1 | 254 | 0 | 45 |
| 55 | 4.26 | 8.52 | AS—Butylester 1.42 | 0.13 | B 0.1 | 2.54 | 0 | 45 |
| 56 | 11.36 | 17.04 | | 0.30 | B 0.2 | 508 | 0 | 45 |
| 57 | 11.36 | 17.04 | O | 0.40 | B 0.2 | 508 | 0 | 45 |
| 58 | 11.36 | 17.04 | O | 2.00 | B 0.2 | 508 | 10 | 45 |
| 59 | 22.72 | 34.08 | O | 0.60 | B 0.4 | 616 | 0 | 45 |
| 60 | 11.36 | 17.04 | O | 2.50 | B 0.2 | 508 | 0 | 45 |
| 61 | 11.36 | 17.04 | O | 1.500 | 2 Lauroylperoxide | 508 | 10 | 80 |
| 62 | 11.36 | 17.4 | O | 0.30 | B 0.2 | 508 | 3 | 45 |

| | Feed mixture | | | | | | | Characteristic data |
|---|---|---|---|---|---|---|---|---|
| No. | AS (g) | AM (g) | Monomer III (g) | TAE (g) | Initiator (g) | t-BuOH (ml) | $H_2O$ (ml) | |
| 45 | 21.3 | 42.6 | IBMA 7.1 | 0.75 | A 1.0 | 440 | 15 | 70/2.77–155 |
| 46 | 21.3 | 46.15 | IBMA 3.55 | 0.75 | A 1.0 | 440 | 15 | 70/2.70–154 |
| 47 | 21.3 | 48.2 | IBMA 1.5 | 0.75 | A 1.0 | 440 | 15 | 70/3.00–150 |
| 48 | 21.3 | 39.76 | IBMA 7.1/ MAS-C18 2.84 | 0.75 | A 1.0 | 440 | 15 | 70/2.90–151 |
| 49 | 102.24 | 153.36 | O | 1.35 | 0.2 Lauroyl- | 477 | 18 | 70/2.42–127 |

-continued

By varying the comonomers, the crosslinker content, the initiator content and the water content the polymers of table III are obtained. Working up is effected in accordance with Example 6.
The following abbreviations are additionally used in table III:
IBMA = Isobutoxymethylene acrylamide
MAS - C18 = Methacrylic acid stearyl ester
AS - Butylester = Acrylic acid butyl ester

| | | | | | peroxide | | | | |
|---|---|---|---|---|---|---|---|---|---|
| 50 | 21.3 | 46.86 | MAS-C18-Ester 2.84 | 0.75 | A 1.0 | | 440 | 15 | 70/2.68–158 |
| 51 | 38.34 | 87.21 | MAS-C18-Ester 2.52 | 1.35 | B 0.1 | 20 ml BuOH | 290 | 4 | 70/2.11–145 |
| 52 | 38.34 | 76.68 | AS—Butylester 12.78 | 1.12 | B 0.1 | 20 ml BuOH | 326 | 18 | 70/2.56–156 |
| 53 | 38.34 | 76.68 | AS—Butylester 12.78 | 1.12 | B 0.1 | 20 ml BuOH | 326 | 0 | 70/2.30–115 |
| 54 | 51.12 | 45.18 | AS—Butylester 31.5 | 1.35 | B 0.1 | 20 ml BuOH | 326 | 0 | 70/2.46–154 |
| 55 | 38.34 | 76.68 | AS—Butylester 12.78 | 1.12 | B 0.1 | 20 ml BuOH | 326 | 0 | 70/2.08–156 |
| 56 | 102.24 | 153.36 | O | 2.70 | B 0.2 | 40 ml BuOH | 612 | 28 | 70/2.09–128 |
| 57 | 102.24 | 153.36 | O | 3.60 | B 0.2 | 40 ml BuOH | 652 | 28 | 70/2.10–152 |
| 58 | 102.24 | 153.36 | O | 0 | B 0.2 | 40 ml BuOH | 652 | 18 | 70/1.97–141 |
| 59 | 90.88 | 136.32 | O | 2.40 | O | | 544 | 28 | 70/1.98–138 |
| 60 | 102.24 | 153.36 | O | 0 | B 0.2 | 40 ml BuOH | 652 | 28 | 70/2.05–156 |
| 61 | 102.24 | 153.36 | O | 0 | 0.2 Lauroyl-peroxide | | 652 | 18 | 70/2.40–117 |
| 62 | 102.24 | 153.36 | O | 2.70 | B 0.2 | 40 ml BuOH | 612 | 25 | 70/2.15–138 |

The following examples illustrate the possible uses of the above copolymers for the preparation of industrial, cosmetic and pharmaceutical products. Examples of these are emulsion-like skin-care and hair-care agents, toothpastes, shaving creams, sun repellants, insect protection agents or hair-styling products. Other fields of use are in the production and preparation of pharmaceutical formulations in the form of tablets, ointments and gels. Because of their consistency-increasing properties, the copolymers can also be used in industrial products which preferably contain solvents, such as vehicle cleaners, engine cleaners and domestic products.

The proportion of copolymers, which are preferably employed in neutralised form, is between 0.02 and 3%, preferably between 0.3 and 2%, based on the weight of the finished product, depending on the desired viscosity.

The polymers, which are usually in non-neutralised form, are, in a manner which is known per se, mixed with the water or water-containing solvent and dispersed and the dispersion is then adjusted to a pH value of between 7 and 10 with the usual neutralising agents, such as sodium hydroxide solution, potassium hydroxide solution, alkanolamines, ammonium hydroxide, fatty amines or mixtures thereof, if appropriate with warming. The other components are added before or after the neutralisation, appropriately before the neutralisation.

The following examples are intended to illustrate the possible uses of the polymeric thickeners.

Ultrasonic diagnosis gel
0.7% of polymer according to Example 34
0.15% of NaOH
5.0% of glycerol to 100% with water+preservative
  Ointment with zinc oxide
0.8% of polymer according to Example 34
1.0% of triethanolamine
12.0% of zinc oxide to 100% with water+preservative
  Furniture polish
0.4% of polymer according to Example 34
0.15% of NaOH
5.0% of silicone oil emulsion (30% strength)
3.0% of carnauba wax emulsion (20% strength) to 100% with water
  Domestic cleaning agent
1.0% of polymer according to Example 34
1.25% of triethanolamine
10.0% of isopropyl alcohol
10.0% of nonylphenol+10 moles of ethylene oxide to 100% with water
  Water-in-oil cream
0.3% of polymer according to Example 34
0.1% of monoethanolamine
4.0% of diglycerol sesquiisostearate
10.0% of paraffin oil
5.0% of cetyl alcohol
2.0% of microwax
0.2% of perfume oil to 100% with water+preservative
  After-shave gel
1.0% of polymer according to Example 34
0.32% of monoethanolamine
35.0% of ethyl alcohol
0.1% of menthol to 100% with water+preservative
  Hair shampoo
0.5% of polymer according to Example 34
0.62% of triethanolamine
12.0% of coconut oil alcohol+10 moles of ethylene oxide
0.1% of perfume oil to 100% with water+preservative
  Hair-setting gel
1.2% of polymer according to Example 34
1.5% of triethanolamine
40.0% of ethyl alcohol
0.1% of perfume oil to 100% with water+preservative
  Liquid oil-in-water emulsion
0.20% of polymer according to Example 34
0.05% of NaOH
5.0% of isopropyl palmitate
5.0% of paraffin oil
5.0% of diglycerol stearate+4 moles of ethylene oxide
0.1% of perfume oil to 100% with water+preservative
  Oil-in-water cream
0.6% of polymer according to Example 34
0.75% of triethanolamine
5.0% of vaseline
5.0% of soybean oil
3.0% of glycerol monostearate
3.0% of tri-stearyl tetraglycol ether ortho-phosphoric acid ester to 100% with water+preservative
  Liquid water-in-oil emulsions
0.2% of polymer according to Example 34
0.6% of ammonium hydroxide (10% strength)

3.0% of hydrogenated castor oil+7 moles of ethylene oxide
6.0% of ®Hostacerin WO (Hoechst AG)
10.0% of isopropyl palmitate
15.0% of perhydrosqualene to 100% with preservative+water The resulting dispersion has the following action data: 70/3.7-125.

The polymers shown in Table 3 are prepared by the same process. In polymers 5-9, the amounts of monomers, tert.-butanol, water, ammonia employed for the neutralisation, emulsifiers and hydrocarbon mixture are doubled.

TABLE 3

| No. | Initial mixture (no feed mixture) | | | | | | | Characteristic data |
|---|---|---|---|---|---|---|---|---|
| | AM (g) | AA (g) | TAE (g) | t.BuOH (ml) | H$_2$O (g) | Init. (g) | Temp. (°C.) | |
| II | 49,7 | 21,3 | 1 | 440 | 15 | 0,5 | 50 | 70/3,4-155 |
| III | 49,7 | 21,3 | 1 | 440 | 15 | 3 | 50 | 70/4,4-120 |
| IV | 49,7 | 21,3 | 1 | 440 | 15 | 1 | 60 | 70/4,0->160 |
| V | 99,4 | 42,6 | 1 | 880 | 30 | 2 | 50 | 70/8,3-66 |
| VI | 99,4 | 42,6 | 1,25 | 880 | 30 | 2 | 50 | 70/5,5-75 |
| VII | 99,4 | 42,6 | 1,5 | 880 | 30 | 2 | 50 | 70/3,7-108 |
| VIII | 99,4 | 42,6 | 1,5 | 880 | 30 | 3 | 50 | 70/6,2-145 |
| IX | 99,4 | 42,6 | 1,5 | 880 | 30 | 1 | 50 | 70/5,5-135 |

COMPARISON EXAMPLE I

The following comparison example and its variations given in Table 3 show that although in the customary polymerisation procedure in which the total amount of all the starting materials is mixed and the reaction is then started it is also possible to vary the properties of the polymers by varying the reaction conditions, it is not possible to prepare products in which a high activity is combined with a low sensitivity towards electrolytes in such an advantageous manner as in the products prepared according to the invention.

440 ml of tert.-butanol and 15 g of deionised water are initially introduced into a reaction vessel equipped with a stirrer, reflux condenser, thermometer, gas inlet tube, dropping funnel and electrically heated waterbath. 49.7 g of acrylamide and 21.3 g of acrylic acid are dissolved therein, with stirring. 1 g of tetraallyloxyethane is added to the solution. While passing in a weak stream of nitrogen, the monomer solution is stirred and the temperature is brought to 50° C. 1 g of azodiisobutyronitrile is added at this temperature. About 10-30 minutes after addition of the catalyst, the polymerisation starts. The polymer thereby precipitates as a white slurry-like mass. The temperature rises to 70°-80° C. in the course of 30-40 minutes. When the polymerisation has ended, that is to say when the reaction temperature has dropped, the mixture is after-heated at an internal temperature of 80° C. for a further 2 hours, with stirring.

When the reaction mixture has cooled to 20° C., it is neutralised by passing in gaseous ammonia. The temperature thereby rises to about 40° C. The reaction flask is equipped with a homogenising apparatus. The polymer dispersion is finely homogenised by pumping several times over the homogenising apparatus.

The reflux condenser is replaced by a distillation bridge and a solution of 3.5 g of a sorbitan fatty acid ester, 4.9 g of an ethoxylated nonylphenol and 1.4 g of an ethylene oxide/propylene oxide block polymer in 119.5 g of an isoparaffinic hydrocarbon mixture with a boiling range of 150° to 350° C. is added dropwise through the dropping funnel. The reaction mixture is at the same time heated to the boiling point, and the solvent tert.-butanol is distilled off completely during the dropwise addition. About 207 g (~100% of theory) of a pourable, non-settling, approximately 37% strength dispersion of the polymer in the hydrocarbon mixture remain.

The above comparision examples show that even the most advantageous conventionally prepared product variants, I, II and VII do not achieve by far the quality of the copolymers prepared according to the invention. The conventionally prepared copolymer IV has only the quality data 70/4→160, and is particularly useless because of its relatively high sensitivity towards electrolytes, and copolymer dispersions III, V, VI and VIII to X no longer give the viscosity of 70 dPas in electrolyte-containing solution, even when more than 4.2% by weight is employed, and are therefore eliminated because their effectiveness is too low for use in practice.

The abovementioned characteristic action data of the products of Embodiment Examples 1 to 12 and of Comparison Examples 1 to X are presented in the graph in FIG. 1. In this presentation, the products are more favourable the further to the left and the further to the bottom their marks are situated. The drastic differences in quality between the products according to the invention and the conventionally prepared products are immediately seen.

The figure is a graph showing viscosity in water of various polymers of this invention and comparitive polymers at various concentration levels.

The conventional products are shown in double circles, and the products according to the invention which are directly comparable to them in respect of their chemical composition are shown in single circles.

Products according to the invention of different chemical composition are in squares. The conventional products shown with an arrow no longer fall within the presentation range of the diagram.

What is claimed is:
1. Process for the preparation of copolymers from acrylamide and acrylic acid or a salt thereof or acrylamide and methacrylic acid or a salt thereof which comprises polymerizing
   (a) 10-90 parts by weight of acrylamide,
   (B) 90-10 parts by weight of acrylic acid, methacrylic acid or of a salt thereof,
   (C) 0-40 parts by weight of a copolymerizable monomer of the formula

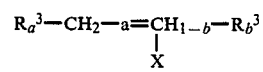

and (D) 0.2–5 parts by weight of a copolymerizable, cross-linking agent which has two or more olefinic double bonds, wherein the polymerization is carried out in a solvent consisting of tert.-butanol containing up to 10% by weight water by precipitation polymerization wherein (i) 10–90% by weight of the tert.butanol solvent,
(ii) 10–90% by weight of the total amount of polymerizing monomers (A), (B) and (C) and
(III) 10–100% by weight of the crosslinker substance (D) are mixed, then polymerization is initiated with an initiator, then the remainder of the reaction components are added as individual components or as a mixture after the polymerization has begun, and thereafter completing polymerization;

wherein $R^3$ is hydrogen or methyl, a and b each are the value 0 or 1 with the sum of a and b also being 0 or 1, and X is of the formula

alkoxycarbonyl with 1 to 20 carbon atoms, hydroxyalkoxycarbonyl with 1 to 3 carbon atoms, N-methylolcarboxamide of the formula HOCH$_2$NH—CO—, N-methylolcarboxamide of the formula HOCH$_2$NH—CO— having the methylol group etherified with alkanols having 1 to 4 carbon atoms, alkanoylamino with 1 to 4 carbon atoms, alkanoylamino with 1 to 4 carbon atoms N-substituted by methylol or alkyl with 1 to 4 carbon atoms, cyano, phenyl, benzyl, imidazol-1-yl, sulphonic acid group or its salts, sulphoalkylamidocarbonyl with 1 to 4 carbon atoms in the alkyl, phosphonic acid group or its salts, phosphonic acid ester of the formula

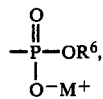

phosphonic acid anhydride of the formula

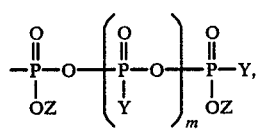

a moiety of the formula

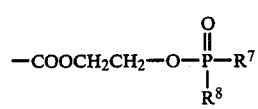

an amino or quaternized amino of the formula

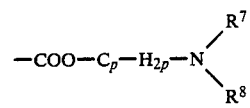

or an amino or quaternized amino of the formula

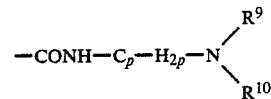

wherein $R^4$ and $R^5$ independently of one another are each hydrogen, methyl or ethyl, or together are trimethylene or pentamethylene, $R^6$ is alkyl with 1 to 4 carbon atoms, Z is alkyl with 1 to 4 carbon atoms, or a cation, m is a number from 0 to 6, Y is a moiety of the formula

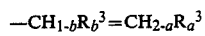

$R^7$ and $R^8$ are identical or different and each is alkyl with 1 to 7 carbon atoms, $R^9$ and $R^{10}$ are identical or different and each is alkyl with 1 to 4 carbon atoms and p is a number from 1 to 4.

2. Process according to claim 1 wherein monomer (C) has the formula

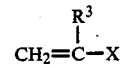

in which $R^3$ is hydrogen or methyl and X has the formula

alkoxycarbonyl with 1 to 20 carbon atoms, hydroxyalkoxycarbonyl with 2 or 3 carbon atoms, sulphonic acid group or its salts, sulphoalkylamidocarbonyl with 1 to 4 carbon atoms in the alkyl, phosphonic acid group or its salts, phosphonic acid ester group of the formula

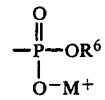

or phosphonic acid anhydride group of the formula

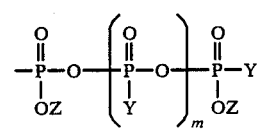

wherein M$^+$ is an alkali metal or ammonium cation.

3. Process according to claim 2 which comprises polymerizing
   (A) 30–70 parts by weight of acrylamide,
   (B) 70–30 parts by weight of acrylic acid or methacrylic acid and 0–20 parts by weight of copolymerizable monomer (C).

4. Process according to claim 1 which comprises polymerizing
   ()A) 30–70 parts by weight of acrylamide,
   (B) 70–30 parts by weight of acrylic acid or methacrylic acid and 0–20 parts by weight of copolymerizable monomer (C).

5. Process according to claim 1 wherein 10 to 50% by weight of the amount of monomers (A), (B) and (C) together with 10 to 100% by weight of the crosslinker substance (D) are dissolved in 10 to 75% by weight of solvent and, after polymerization has been started with 10 to 100% by weight of the initiator, the remainder of solvent, monomers, cross-linking agent and initiator are metered in to the mixture.

6. Process according to claim 5 wherein 10 to 20% by weight of the amount of monomers (A), (B) and (C) are initially dissolved in 10 to 50% by weight solvent.

7. Process according to claim 1 wherein 10 to 50% by weight of the total amount of crosslinking agent (D) to be copolymerized is initially introduced and the remainder is metered in to the mixture during the polymerization.

8. Process according to claim 1 wherein the cross-linking agent (D) amount to 0.2 to 2 parts by weight.

* * * * *